United States Patent
Randolph

(10) Patent No.: US 9,448,230 B2
(45) Date of Patent: Sep. 20, 2016

(54) METHOD OF HEMOGLOBIN-F DETERMINATION

(71) Applicant: Saint Louis University, St. Louis, MO (US)

(72) Inventor: Timmy Ray Randolph, Collinsville, IL (US)

(73) Assignee: Saint Louis Univeristy, St. Louis, MO (US)

( * ) Notice: Subject to any disclaimer, the term of this patent is extended or adjusted under 35 U.S.C. 154(b) by 0 days.

(21) Appl. No.: 14/443,676

(22) PCT Filed: Nov. 21, 2013

(86) PCT No.: PCT/US2013/071234
§ 371 (c)(1),
(2) Date: May 19, 2015

(87) PCT Pub. No.: WO2014/081933
PCT Pub. Date: May 30, 2014

(65) Prior Publication Data
US 2015/0323521 A1 Nov. 12, 2015

Related U.S. Application Data

(60) Provisional application No. 61/729,258, filed on Nov. 21, 2012.

(51) Int. Cl.
*G01N 33/72* (2006.01)
*G01N 33/50* (2006.01)
*G01N 33/49* (2006.01)

(52) U.S. Cl.
CPC ........ *G01N 33/5094* (2013.01); *G01N 33/721* (2013.01); *G01N 33/491* (2013.01); *G01N 2800/22* (2013.01); *Y10T 436/25375* (2015.01)

(58) Field of Classification Search
CPC .... G01N 33/48; G01N 33/49; G01N 33/491; G01N 33/52; G01N 33/72; G01N 33/721; G01N 33/5091; G01N 33/5094; G01N 2800/22; Y10T 436/25; Y10T 436/25375
USPC ........ 436/63, 66, 164, 174, 177; 422/72, 73, 422/82.05, 82.09, 527, 533; 435/29
See application file for complete search history.

(56) References Cited

U.S. PATENT DOCUMENTS

| | | | |
|---|---|---|---|
| 2,171,961 | A | 9/1939 | Fortune |
| 3,761,226 | A | 9/1973 | Louderback et al. |
| 3,847,545 | A | 11/1974 | Shanbrom et al. |
| 8,623,659 | B2 | 1/2014 | Randolph |
| 2006/0068375 | A1 | 3/2006 | Tsipouras et al. |
| 2006/0072805 | A1* | 4/2006 | Tsipouras ............... G01N 1/312 382/134 |
| 2010/0159506 | A1 | 6/2010 | Parikh et al. |
| 2011/0294114 | A1 | 12/2011 | van Der Loo et al. |
| 2012/0077218 | A1 | 3/2012 | Randolph |

OTHER PUBLICATIONS

Sigma-Aldrich, Revised: Jan. 2005, "Fetal Hemoglobin" (Procedure No. 285) www.sigmaaldrich.com.
Randolph and Schumacher (2012) "A Method of HbF Determination for Potential Use in Underdeveloped Countries" vol. 25, No. 4 Fall 2012 Clinical Laboratory Science.
European Patent Office (International Searching Authority), International Search Report and Written Opinion for PCT/US2013/071234 (filed Nov. 21, 2013); Date of Mailing: Feb. 7, 2014.
Randolph, Tim R.: "Estimated Prevalence of Sickle Cell in Northern Haiti.", Clinical Laboratory Science: Journal of American Society for Medical Technology Spring 2010 LNKD-PubMed: 20499530, vol. 23, No. 2, Apr. 2010, pp. 79-83, XP009154550, ISSN: 0894-959X entire document.
Anonymous: "Sickle-STAT: A Qualitative Test Kit for the Determination of the Presence of Hemoglobin S in Human Blood", Chembio Diagnostic Systems, Inc. Internet, May 1, 2006, pp. 1-3, XP002665027, Retrieved from the Internet: URL:http://www.surecheck.com/pdfs/6172%20Sickle-STAT%20SC%20901%20Product%20Insert%20Rev%203.pdff [retrieved on Dec. 2, 2011] entire document.
Randolph, Tim R: "Determining the Usefulness of the Modified Hemoglobin Solubility Test in Diagnosing Infants with Homozygous Sickle Cell Anemia" Clinical Laboratory Science: Journal of the American Society for Medical Technology Summer 2008, vol. 21, No. 3 Jun. 2008, pp. A2, A3-A129, 141, XP002665025, ISSN: 0894-959X Retrieved from Internet: URL:http://www.ascls.org/resource/resmgr/Value-Publications/CLS_Vol_21_3_2008_final.pdf.pdf [retrieved on Dec. 2, 2011] entire document.
Huntsman et al., A rapid whole blood solubility test to differentiate the sickle-cell trait from sickle-cell anaemia. Journal of Clinical Pathology, vol. 23,1970, pp. 781-783.
Sunderman et al., Ancillary tests for identification of abnormal hemoglobins. I. The measurement of ferrohemoglobin solubility (modification of the Itano-Goldberg procedure) Hemoglobin, Precursors Metab. (1964) 109-10.
Randolph and Schumacher (2012) "A Method of HbF Determination for Potential Use in Underdeveloped Countries" vol. 25, No. 4 Fall 2012 Clinical Laboratory Science—Abstract ncbi.nlm.nih.gov/pubmed/23330510.

* cited by examiner

*Primary Examiner* — Maureen Wallenhorst
(74) *Attorney, Agent, or Firm* — Randolph Bretton; The Law Office of Randolph Bretton

(57) ABSTRACT

The Inventors disclosed an inexpensive method of determining fetal hemoglobin (HbF) in red blood cells of individuals with sickle cell anemia undergoing hydroxyurea treatment. The method is based on the specific elution and measurement of sickle hemoglobin (HbS) from red blood cells, wherein the amount of HbF may be determined according to the formula: HbF=Total hemoglobin−HbS. The method may also be used to determine the amount of HbF in individuals without sickle cell anemia by the specific elution of adult or normal hemoglobin (HbA) from red blood cells whereby the amount HbF may be determined according to the formula: HbF=Total hemoglobin−HbA. The method will also determine levels of HbS or HbA in individuals with sickle cell and without sickle cell respectively. The methods have the advantage of being easy to practice in underdeveloped countries.

20 Claims, 6 Drawing Sheets

METHOD OF HEMOGLOBIN-F DETERMINATION

CROSS REFERENCE TO RELATED APPLICATIONS

This application claims priority to provisional application 61/729,258, filed Nov. 21, 2012, hereby incorporated by reference in its entirety.

FIELD OF THE INVENTION

The invention relates to methods and compositions for measuring adult, sickle, and fetal hemoglobin in normal individuals and patients with sickle cell who are receiving hydroxyurea therapy.

BACKGROUND

Sickle cell anemia is one of the most commonly inherited genetic diseases, annually affecting approximately 275,000 births worldwide (Modell et al., (2008) Bull World Health Organ.: 86:480-7). The disease is most prevalent in African countries and countries in which a large proportion of the population is of African descent, such as the Caribbean nation of Haiti. In Western Africa, 1.7% of children are born with the disease, and in the Caribbean, the percentage is 0.4%. Id. In particular, the prevalence of sickle hemoglobin (HbS) in Haiti, representing both homozygotes and heterozygotes, is 15.2%. (Randolph (2010) Clin Lab Sci.; 23:79-83)

Sickle cell syndromes result from a single point mutation causing the substitution of valine for glutamic acid at position six of the β-globin chains, producing HbS ($\alpha 2\beta 2s$) instead of normal hemoglobin, HbA ($\alpha 2\beta 2$). (Pauling et al. (1949) Science.; 110:543-8; Marotta et al. (1977) J Biol Chem; 252:5040-53; Ingram (1959) Biochim Biophys Acta.; 36:402-11) The sickle cell β-globin gene must be inherited in the homozygous state for this mutation to result in sickle cell disease (SCD). The heterozygous state produces sickle cell trait (SCT) and few, if any, complications. Other clinical conditions involving the sickle cell gene can occur in individuals inheriting one sickle cell allele with a β-thalassemia allele or another β-chain hemoglobinopathy (compound heterozygotes) (Steinberg. (2008) The Scientific World Journal.; 8:1295-1324).

The clinical symptoms of SCD stem from a change in the intracellular polymerization of HbS when in the deoxyhemoglobin form (Eaton and Hofrichter (1990) Adv Protein Chem.; 40:63-279). This altered polymerization results in sickle-shaped red blood cells (RBCs), which become trapped in the microvasculature and cause hypoxia, tissue death, and the severe pain associated with sickle cell crises. In addition, extravascular and intravascular hemolysis causes hemolytic anemia. A host of other complications are also present that, together, will lead to early death if left untreated. (Steinberg. (2008) The Scientific World Journal.; 8:1295-1324)

Established treatments for SCD involve infection prophylaxis, pain management, and blood transfusion with iron chelation (Ballas Drugs. (2002); 62:1143-72). A more recent approach to treatment involves the drug hydroxyurea to increase expression of fetal hemoglobin (HbF), which proportionately reduces the percentage of HbS. HbF ($\alpha 2\gamma 2$) interrupts HbS polymerization, preventing formation of sickle cells and reducing the frequency of vaso-occlusive events. (Goldberg et al., (1977) J Biol Chem.; 252:3414-21).

Hydroxyurea is relatively inexpensive, administered orally, shown to be effective by clinical trials, and is the only HbF-inducing drug currently approved by the U.S. Food and Drug Administration for treatment of SCD. (Charache et al. (1995) N Engl J Med.; 332:1317-22; Ballas et al. (2006) Health Qual Life Outcomes.; 4:59; Steinberg et al. (2003) JAMA; 289:1645-51) However, the drug also presents challenges. Sickle cell patients exhibit a wide range of baseline HbF levels; and when treated with hydroxyurea, the magnitude of their HbF response also varies widely. (Charache et al. (1995) N Engl J Med.; 332:1317-22.; Steinberg et al. (1997) Blood; 89:1078-88) It is estimated that 10-20% of patients show no increase in HbF levels (Steinberg. (2008) The Scientific World Journal.; 8:1295-1324). Since hydroxyurea is mildly carcinogenic, HbF levels must be monitored during treatment to determine the minimum effective dosage or to stop the drug in non-responders. (Ballas Drugs. (2002); 62:1143-72; Ferster et al., (2003) Br J Haematol.; 368-9.)

In developed countries, HbF levels are monitored by electrophoresis or HPLC, but these methods are impractical in underdeveloped countries. Spectrophotometric methods of HbF measurement based upon the resistance of HbF to alkali denaturation have been described, but these methods are limited by method complexity and the need for transport, handling, and storage of a caustic base (NaOH or KOH) and potassium cyanide (KCN). (Singer et al., (1951) Blood; 6:413-28; Betke K, et al., (1959) Nature; 184:1877-8; Pembrey et al., 1972 J Clin Pathol.; 25:738-40; Serjeant et al., 1975 J Clin Pathol.; 28:761-4) One method, the Kleihauer-Betke test (K-B test), is used to determine the presence or absence of HbF-containing RBCs in a blood smear. It is based on the elution of HbA or HbS in citric acid solutions. However, the K-B test is not able to make quantitative determinations of HbF.

The Inventor discloses herein, a simple inexpensive method of monitoring HbA, HbS, or HbF in a quantitative manner, that may be used to monitor patients with sickle cell anemia undergoing hydroxyurea therapy and may be easily practiced in underdeveloped countries,

SUMMARY

One embodiment of the invention is a method for determining the amount of Fetal hemoglobin (HbF) in the red blood cells of individual with sickle cell anemia undergoing hydroxyurea treatment, by determining the amount of sickle cell hemoglobin (HbS) eluted from the individual's red blood cells in an acidic solution, by spectrophotometric analysis, determining the amount of total hemoglobin, and determining the amount of HbF according to the formula, HbF=Total hemoglobin−HbS.

Another embodiment of the invention is a method for determining the amount of HbF in the red blood cells of individual without sickle cell, by determining the amount of adult or normal hemoglobin (HbA) eluted from the individual's red blood cells in an acidic solution, by spectrophotometric analysis, determining the amount of total hemoglobin, and determining the amount of HbF according to the formula, HbF=Total hemoglobin−HbA.

Another embodiment of the invention is a method for determining the amount of HbF in the red blood cells of individual by determining the amount of adult or normal hemoglobin (HbA) or sickle hemoglobin (HbS) eluted from the individual's red blood cells in an acidic solution, by spectrophotometric analysis, and determining the amount of HbF concentration as the inverse of the absorbance value after first standardizing the amount of hemoglobin introduced into the test system using a hemoglobin or hematocrit value and adjusting the volume of blood used.

In yet another embodiment of the invention is a method for determining the amount of HbS in the red blood cells of an individual with sickle cell anemia undergoing hydroxyurea treatment, wherein the amount of HbS, is the amount eluted from the individual's red blood cells in an acidic solution and determined by spectrophotometric analysis.

In yet another embodiment of the invention is a method for determining the amount of HbA in the red blood cells of an individual without sickle cell anemia, wherein the amount of HbA is the amount eluted from the individual's red blood cells in an acidic solution and determined by spectrophotometric analysis.

DEFINITIONS

Figure 1:
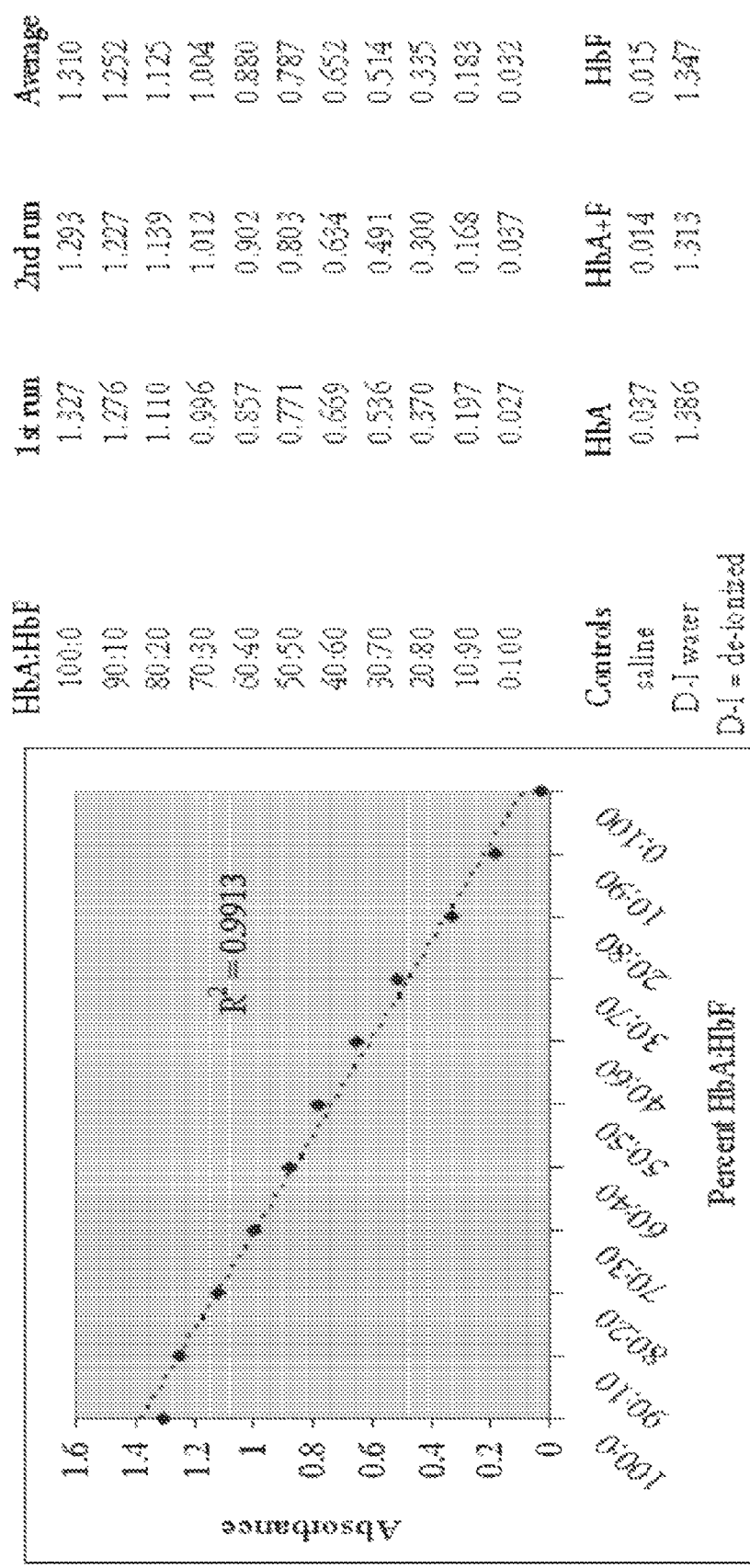
FIG. 1 illustrates absorbance values of samples with decreasing HbA percentage and increasing HbF percentage.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements. The word "or" means any one member of a particular list and also includes any combination of members of that list, unless otherwise specified.

The term "about" is used herein to mean approximately, roughly, around, or in the region of. When the term "about" is used in conjunction with a numerical range, it modifies that range by extending the boundaries above and below the numerical values set forth. Preferably, the term "about" is used herein to modify a numerical value above and below the stated value by a variance of 20 percent up or down (higher or lower).

An "individual" is a vertebrate, preferably a mammal, more preferably a human. Mammals include, but are not limited to, farm animals (such as cows), sport animals, pets (such as cats, dogs, and horses), primates, mice, and rats.

DESCRIPTION OF PREFERRED ASPECTS OF THE INVENTION

In one aspect, there is provided a simple and cost-effective method of quantitative fetal hemoglobin (HbF) measurement using non-hazardous reagents and suitable for laboratories in underdeveloped countries that are involved in sickle cell testing and hydroxyurea treatment. The assay is based on the selective elution of adult and sickle hemoglobin from red blood cells in acidic solutions.

Normal newborn individuals produce high levels of HbF and low levels of adult or normal (HbA). Within the first few months HbF is replaced by HbA. Sickle cell patients produce an abnormal type of hemoglobin in place of HbA, which has been designated HbS. Newborn sickle cell individuals will have high levels of HbF, low HbS, and no HbA. Around 3-6 months HbS levels rise and HbF levels fall. HbA is not produced. By 1-2 years HbS levels are >90% (often 95-99%) with the balance being HbF and a small amount of HbA2. Since there are largely only two types of hemoglobin present, in either a normal or sickle cell individual, the amount of HbF is inversely proportionate to HbA in normal individuals or HbS in sickle cell individuals.

The method of HbF determination is based on a spectrophotometric determination of HbA or HbS from red blood cells compared to total hemoglobin in a test sample. In one embodiment, a test sample of whole blood from an individual is introduced into an acidic solution. The acidic conditions result in the specific elution of HbA or HbS from the red blood cells. In normal individuals, HbF may be calculated according to the formula, HbF=Total hemoglobin−HbA. In sickle cell individuals, HbF may be calculated according to the formula, HbF=Total hemoglobin−HbS. There are numerous methods in which to calculate total hemoglobin. In one non-limiting example, a parallel sample may be introduced into distilled water which will result in complete hemolysis and release of total hemoglobin. Levels of HbA, HbS, and total hemoglobin in solution may be determined spectrophotometrically in reference to a standard curve.

In another non-limiting embodiment, the amount of hemoglobin in samples taken from an individual and introduced in to the acidic solution may be standardized based on a reading from a hematocrit or similar technology. If desired, reference samples, including samples used to produce a standard curve may also be prepared with corresponding hematocrit values. Since HbF together with either HbA or HbF represent total hemoglobin, and HbF levels are inversely proportional to HbA or HbS levels and total hemoglobin between samples are equal, then an absorbance reading for HbA or HbS may be representative of a value for HbF.

Numerous applications for this method are envisioned. In one non-limiting embodiment, an application of the method will be to monitor patients with sickle cell anemia undergoing hydroxyurea treatment. A sample containing red blood cells is taken from an individual (e.g. blood, bodily fluid, or bodily tissue), such as a patient suffering from sickle cell anemia and being treated with hydroxyurea. The sample is added to a buffer solution, to form a first mixture. The first mixture is left to incubate for a set incubation time and is then centrifuged to form a solid deposit containing RBCs and a supernatant. The absorbance of the supernatant is measured spectrophotometrically, and amounts of HbS are determined by comparing the absorbance reading, to a standard reference curve. Amounts of HbF are calculated, by subtracting the amount of HbS, from total hemoglobin in the sample. The amount or percentage of HbF present in the sample may be used by the treating physician as an indicator of the effectiveness or ineffectiveness of the patient's ongoing treatment with hydroxyurea.

It is also envisioned that the treating physician may use any information generated by the method to monitor the patient. By way of example, a trend of increasing or decreasing level of HbS may also be used by the treating physician as an indicator the effectiveness or ineffectiveness of a patient's ongoing hydroxyurea therapy.

In another non-limiting embodiment, HbA levels may be measured to determine HbF levels in the blood of post-delivery maternity patients, in order to determine whether fetal blood was introduced back into mother's circulation during delivery, which may create the possibility of serious complications during subsequent pregnancies.

The buffer solution used to form the first mixture has a preferred pH in the range of about 3.1 to about 3.3; the most preferred being a pH of 3.3. However it is anticipated that a solution with a pH in the range of 3.1 to 3.5 would be may also be used. A preferred buffer is prepared from 0.07 M sodium citrate and 0.06 M sodium phosphate buffer. This may be attained from a premeasured kit, by way of example, the commercially available Citrate Phosphate Buffer commonly used in the K-B test. In a preferred embodiment, a concentration of 0.07 M sodium citrate and 0.06 M sodium phosphate was found to produce the best results.

The length of the incubation time is preferably one which maximizes the elution of HbA or HbS, minimizes the elution of HbF, and produces absorbance readings exhibiting a linear dependence with respect to HbA or HbS concentration. In preferred embodiments, where a Citrate Phosphate Buffer is used, and the incubation is conducted at a temperature of about 37° C., an incubation time of about 6 minutes has been found to yield best results.

Centrifugation methods are well known in the art. The centrifugation step is preferably conducted for a length of time which is the shortest and/or using an rpm which is the lowest, which results in the separation of the first mixture into a solid residue and a supernatant. With regard to the absorbance reading of the supernatant, it has been found that hemoglobin eluted into acidic media produces a brown color, rather than the usual red hue seen in neutral aqueous solutions. Accordingly, the optimum wavelength may vary depending on the pH of the buffer solution. In the preferred embodiment, absorbance readings may be taken at a wavelength of 375 nm to about 415 nm, and are preferably taken at a wavelength in the range of about 393 nm to about 397 nm, and most preferably at a wavelength of about 395 nm. The absorbance reading is then compared to a reference curve based on known relative absorbance values and concentrations of HbA and HbF, such as the linear plot of FIG. 1. Based on this correlation, and the amount of total hemoglobin in the sample, a quantitative measurement of the HbF present in the sample is made, thereby enabling physicians or other care-givers to determine whether the patient is responsive to hydroxyurea-based treatments.

For the purposes of calculating HbF, total hemoglobin may be determined by any number of methods. In one non-limiting example, a method preferred for its simplicity and utilization of the same methodology, is performed by preparing a parallel sample containing red blood cells in deionized water, which will result in 100 percent hemolysis of the red blood cells, thereby releasing total hemoglobin into solution. Total hemoglobin may then be determined spectrometrically by measuring the absorbance of the sample and comparing the reading to a standard reference curve, in a manner similar to that descried for determinations of HbA and HbS.

Another non-limiting method of calibrating the absorbance reading of HbA or HbS to a HbF value, would be to standardize the amount of hemoglobin introduced into the citrate or buffer solution by adjusting the blood volume used based, on the basis of a hemoglobin or hematocrit measurement. This may eliminate or reduce differences in initial hemoglobin levels between individuals and/or between samples and to correlate absorbance readings to HbA or HbS levels which are inversely proportional to HbF levels. A hematocrit or similar technology may be used to measure total hemoglobin in the test samples and/or samples prepared to produce a standard reference curve. The volume of RBCs may be adjusted so that equivalent amounts of hemoglobin are compared.

EXAMPLES

To order to demonstrate the accuracy of the method to selective measure adult or normal hemoglobin (HbA) in a sample containing both HbA and fetal hemoglobin (HbF), samples were prepared by containing known amounts of both HbA and HbF. Blood samples from normal individuals (source of HbA) and normal umbilical cord blood (source of HbF) were combined.

In addition, because levels of HbA in normal individuals or levels of sickle hemoglobin (HbS) in sickle cell patients are inversely proportional to levels of HbF, and sickle cell individuals undergoing hydroxyurea treatment present a range of results with respect to HbS and HbF levels, an evaluation of the linearity of the method was performed. Samples were prepared to simulate a set of sickle cell patients undergoing hydroxyurea treatment with a full range of responses, represented by HbA:HbF ratios in 10 percent increments from 0 to 100 percent. This was done by combining increasing ratios of normal adult human blood (source of HbA) and human umbilical cord blood (source of HbF).

To order to demonstrate the accuracy of the method to selectively measure hemoglobin from sickle cell individuals (HbS) in a sample containing both sickle cell hemoglobin (HbS) and fetal hemoglobin (HbF), samples were prepared containing known amounts of both HbS and HbF. Blood samples from sickle cell individuals (source of HbS) and normal umbilical cord blood (source of HbF) were combined. To simulate a set of sickle cell patients undergoing hydroxyurea treatment with a full range of HbS and HbF responses, and to demonstrate the linearity of the method when using samples containing HbS and HbF, samples containing HbS:HbF ratios in 10 percent increments from 0 to 100 percent, were prepared. This was done by combining increasing ratios of sickle cell blood (source of HbS) and human umbilical cord blood (source of HbF).

Materials and Methods

Materials and Equipment

Citrate Phosphate Buffer Solution (0.07 M sodium citrate and 0.06 M sodium phosphate) was prepared from a Fetal Hemoglobin kit (Sigma-Aldrich Fetal Hemoglobin. Procedure No. 285. Revised 2005-01; Sigma-Aldrich, St. Louis, Mo.).

Junior Model 35S spectrophotometer (Perkin-Elmer, Waltham, Mass.)

QuickGel Alkaline hemoglobin electrophoresis system (Helena, Beaumont, Tex.)

Specimens

Normal whole blood samples (source of HbA) were collected by standard venipuncture technique from members of the research team. De-identified whole cord blood samples (source of HbF) were obtained from Cardinal Glennon Pediatric Research Institute, St. Louis, Mo. Specimens were obtained weekly, and only non-hemolyzed specimens were accepted. To standardize the amount of hemoglobin, hematocrits of all test samples were adjusted to 35%. The hematocrit of the normal blood sample and the cord blood sample were adjusted so each had a hematocrit of 35%, in order to ensure that each of the 11 samples (100/0, 90/10, 80/20, etc.) had a hematocrit of 35% and that the absorbance readout was a reflection of HbA elution and not a reflection of HbA elution plus variability in the amount of hemoglobin in the starting sample. When normal and cord blood samples were to be mixed, the cord blood ABO type was determined, and a normal sample was collected from a compatible member of the research team.

Development of Procedure

A procedure was developed in an effort to determine whether HbA elution in solution could be used to produce a reliable method of quantitative measurement. A solution of sodium citrate, 0.7 mol/L, and sodium phosphate, 0.6 mol/L, was prepared weekly. In this example, 4 mL of buffer solution was pipetted into three labeled 12×75 mm test tubes. These were placed into a dry heat block incubator for 15 minutes at 37° C., and then three specimens: (1) normal blood (HbA); (2) a 50:50 mixture of normal and cord blood (HbA+HbF), and (3) cord blood (HbF), were added to the pre-warmed aliquots. After a carefully timed incubation as described below, the tubes were centrifuged at 3,100 rpm to pellet the RBCs. Approximately 3 mL of supernatant was transferred to clean tubes, avoiding the RBC pellet, and measured spectrophotometrically, using a Citrate Phosphate Buffer Solution as a blank.

Analysis was also performed on six control tubes with each experiment: three controls containing HbA, HbA+HbF, or HbF in 4 mL saline (0% hemolysis), and three controls as above in 4 mL de-ionized water (100% hemolysis).

Method Conditions

Wavelength: The wavelength used in the method was determined by performing a spectral scan using the eluate of an HbA sample to determine maximum absorbance wavelengths.

Centrifugation Time: Minimum centrifugation time was determined by adding each of the above three sample types to 4 mL of Citrate Phosphate Buffer Solution, incubating, and testing centrifugation times of 5 minutes, 1 minute, 30 seconds, and 15 seconds. The RBC pellets that formed at each centrifugation time were observed during transfer of supernatant, and the minimum centrifugation time required for the pellets to remain solid was determined.

Incubation Time: The three sample types were incubated in 4 mL of Citrate Phosphate Buffer Solution in one minute intervals from 4 to 10 minutes, in an effort to find an incubation time that maximized elution of HbA, minimized elution of HbF, gave distinctly separate absorbance values for the three sample types, and produced linear results.

Sample Volume: Different volumes of HbA blood, from 10 to 30 μL in increments of 5 μL, were tested in the acid elution procedure until a maximum absorbance value of approximately 1.3 was obtained (upper end of the spectrophotometer's linear range).

Citrate Phosphate Buffer Concentration: When prepared as indicated in the Sigma-Aldrich Fetal Hemoglobin kit (Sigma-Aldrich Fetal Hemoglobin. Procedure No. 285. Revised 2005-01), Citrate Phosphate Buffer Solution contains 0.07 M sodium citrate and 0.06 M sodium phosphate. To determine if this concentration was appropriate for this method of HbF determination, the buffer solution was serially diluted three times, and the three sample types were tested using each dilution.

Evaluation of Reproducibility: To demonstrate reproducibility, a total of 39 runs of the three sample types were performed across two days using the optimized procedure. The same samples and the same batch of buffer solution were used for all runs.

Evaluation of Linearity: Linearity of the optimized procedure was determined by testing different HbA:HbF mixtures in 10% increments, ranging from a ratio of 100:0 to 0:100. This experiment was performed twice, keeping all variables the same. Hemoglobin electrophoresis was performed on the various mixtures to confirm that linearity displayed in the experiment corresponded to the HbA:HbF ratios in the mixtures.

Data Analysis

Using the statistical software SPSS 17.0, reproducibility was determined by analyzing mean absorbance values and standard deviations of the HbA, HbA+HbF, and HbF samples tested. In addition, a one-way ANOVA test and Tukey's HSD post-hoc test were used to show significance of the differences between absorbance values of each sample type. To analyze linearity, Microsoft Excel 2003 was used to average the absorbance values of each HbA:HbF ratio and calculate the coefficient of determination (r2).

Results

Determination of the above described method conditions resulted in the following preferred conditions: a wavelength of 395 nm, a centrifugation time of 30 seconds, a sufficient time for incubation of 6 minutes, a blood volume of 20 μL, and a Citrate Phosphate Buffer concentration of 0.07 M sodium citrate and 0.06 M sodium phosphate with a volume of 4 milliliters.

While examining reproducibility of the method, it was noted that supernatants of the HbA tubes were darkest in color and HbF tubes were lightest in color, the latter often appearing colorless. In addition, the RBC pellets in the HbA tubes were 3 mm in diameter and brown in color, the pellets in the HbA+HbF tubes were 4 mm and red-brown in color, and the HbF tube pellets were 5 mm and red. The three sample types gave distinct mean absorbance values and low standard deviations within and across both days of reproducibility testing, as shown by the low p-values ($<1\times10^{-6}$) of the ANOVA and Tukey's HSD post-hoc tests. (Table 1) An ANOVA statistic was selected to compare mean values of the three absorbance readings because it would not increase the risk of type I error, whereas performing three separate T-tests would artificially increase the alpha producing type I error. The p-value was lower than the $\alpha$ ($<1\times10^{-6}$) indicating that a statistically significant difference exists between at least one mean value pair. A post-hoc test such as Tukey's HSD must be performed following a statistically significant ANOVA to determine which mean value pairs are statistically different. In the present case, each mean absorbance value was statistically different from the other two mean absorbance values.

TABLE 1

Reproducibility Data Within Days and Across Days

| | HbA | HbA + F | HbF |
|---|---|---|---|
| Mean and Standard Deviation Within Day 1 (N = 20) | | | |
| Mean | 1.260 | 0.681 | 0.034 |
| SD | 0.072 | 0.048 | 0.006 |
| Saline control | 0.019 | 0.021 | 0.017 |
| Water control | 1.349 | 1.286 | 1.281 |
| Mean and Standard Deviation Within Day 2 (N = 19) | | | |
| Mean | 1.311 | 0.699 | 0.035 |
| SD | 0.056 | 0.050 | 0.005 |
| Saline control | 0.014 | 0.015 | 0.019 |
| Water control | 1.361 | 1.396 | 1.429 |

TABLE 1-continued

Reproducibility Data Within Days and Across Days

Overall Mean and Standard Deviation Across Days (N = 39)

| | | | |
|---|---|---|---|
| Mean | 1.285 | 0.690 | 0.035 |
| SD | 0.069 | 0.050 | 0.005 |

Comparison of Means

| | |
|---|---|
| One-Way ANOVA Tukey's HSD Post-Hoc | p-value $<1 \times 10^{-6}$ |
| HbA vs HbA + F | p-value $<1 \times 10^{-6}$ |
| HbA vs HbF | p-value $<1 \times 10^{-6}$ |
| HbA + F vs HbF | p-value $<1 \times 10^{-6}$ |

Evaluation of Linearity

Figure 2:
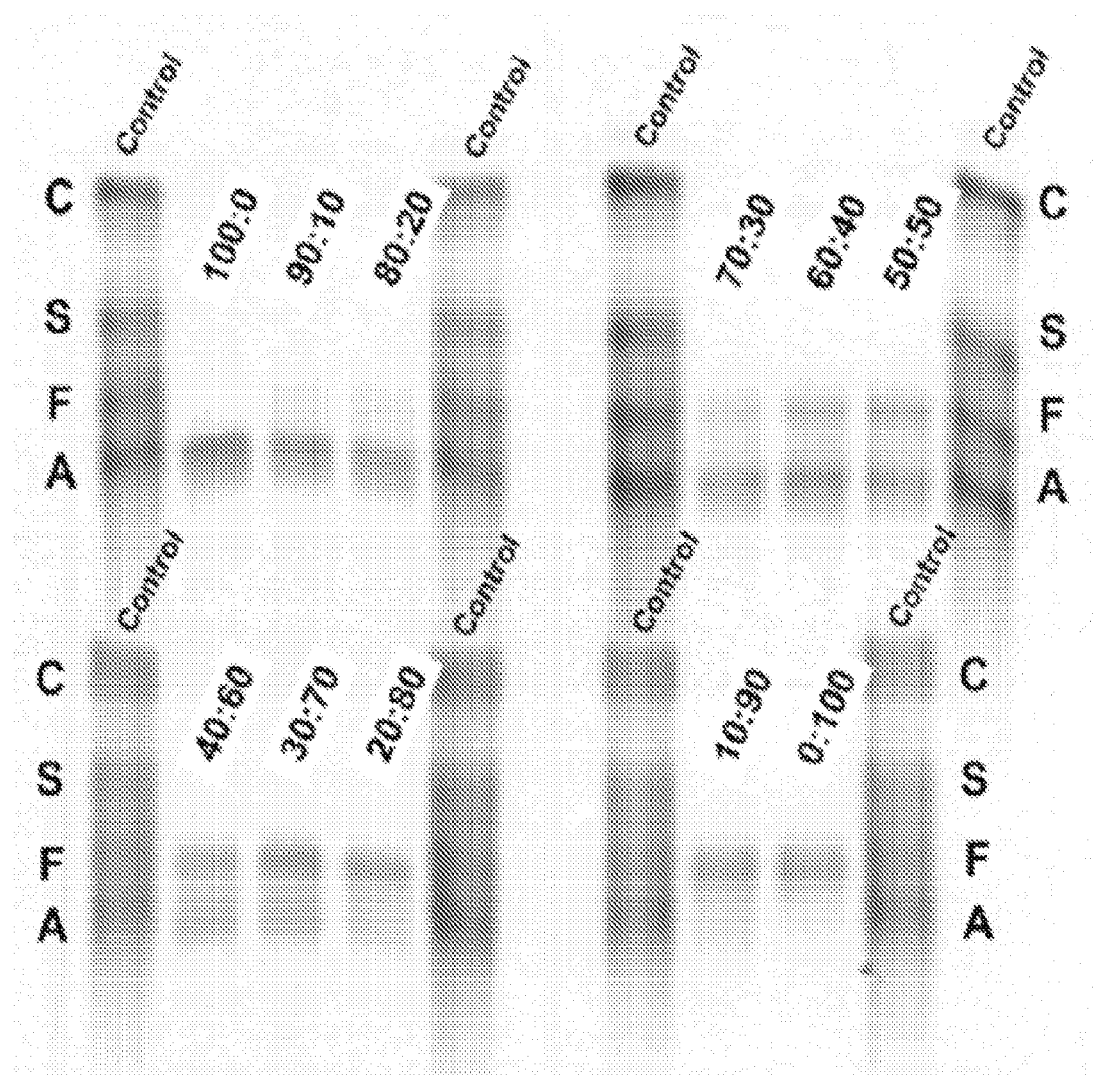
FIG. 2 illustrates gel electrophoresis of HbA:HbF ratio samples.

During the linearity determination, supernatant color decreased proportional to decreasing HbA and increasing HbF concentrations in the HbA:HbF ratio tubes ranging from 100:0 to 0:100. This linear decrease of HbA in the supernatant was visually obvious, and the average absorbance values from the two consecutive experiments produced an r2 value of 0.99. (FIG. 1) Visual inspection of the electrophoresis gel showed that the HbA:HbF mixtures demonstrated expected gradual decrease in HbA banding intensity and proportional increase in HbF banding intensity. (FIG. 2)

Discussion

Example 1 demonstrates a method of selectively eluting HbA from intact RBCs using a citrate buffer solution, while retaining HbF intracellularly. Absorbance of eluted HbA was measured spectrophotometrically and was shown to be proportional to the amount of HbA in the original blood sample. Since HbF is inversely proportional to HbA, levels of HbF may be calculated from a determination of HbA in blood cells of normal patients. By way of example, amounts or percentages of HbF may be calculated by subtracting HbA from total hemoglobin. The method follows the assumption that in RBCs from normal individuals, the only other hemoglobin present in appreciable amounts is HbF. Although other types of hemoglobin may be present, it is not expected that they are abundant enough to affect the clinical interpretation of the results or the analysis.

As outlined above, this method is based on the principle of the presence or absence of HbF-containing RBCs, and the elution of HbA in citric acid solution. It is also recommend that the Citrate Phosphate Buffer Solution be pre-warmed at 37° C. to achieve maximum elution.

Saline and de-ionized water were used in place of Citrate Phosphate Buffer Solution as controls to determine background hemolysis (saline) and maximum hemolysis (water). Saline controls accounted for natural hemolysis occurring in the test system, and de-ionized water controls predicted maximum absorbance should complete elution of all hemoglobin in the RBCs occur. This de-ionized water controls may also be used to determine total hemoglobin for the purposes of calculating HbF. Although the control tubes served the intended purpose, they were not ideal because free hemoglobin in the control tubes produced a red supernatant (although the saline controls were essentially colorless), whereas eluted hemoglobin exposed to acidic buffer in the experiment produced a brown color. Therefore, absorbance values of the controls did not perfectly parallel absorbance values of the experimental tubes because wavelengths used in this study were optimized for brown-colored hemoglobin solutions, not red hemoglobin solutions. This may have specifically affected sensitivity of the saline controls in detecting small amounts of natural hemolysis. Although the controls were imperfect, they served their purpose of ruling out major errors in technique because the saline controls consistently showed low absorbance values similar to HbF blood samples, and the de-ionized water controls consistently showed high absorbance values similar to HbA blood samples.

Centrifugation time proved to be an important component of developing the procedure. A 30-second centrifugation time, which was shorter than the centrifugation time used initially, allowed better delineation between the HbA, HbA+HbF, and HbF samples and better reproducibility of absorbance values. Without being bound to any particular theory, one possible explanation is that co-elution of HbF with HbA occurred during longer centrifugation and that longer exposure to centrifugal forces caused additional hemolysis. Both of these phenomena would increase absorbance of HbF and HbA+HbF samples to a greater degree than HbA samples, causing poor delineation between the samples' absorbance values.

Using the 30-second centrifugation time, incubation intervals from 4 to 10 minutes were tested. The 4, 5, and 5.5-minute incubation times gave lower HbA sample absorbance values than longer incubation times, suggesting that elution of HbA was incomplete. Absorbance values of the HbA samples quickly leveled off after 6 min of incubation. Compared to shorter incubation times, 7 minute incubation showed a slightly higher absorbance in the HbF tubes, and HbF sample absorbance rose dramatically at 8 minutes, suggesting that HbF was co-eluted during longer incubation times. Therefore, 6 minutes was the optimal incubation time because it represented nearly complete elution of HbA, minimal elution of HbF, and excellent delineation and good linearity of the HbA, HbA+HbF, and HbF samples based on absorbance values.

The volume of blood used in the test system was optimized to prevent absorbance values from being above linearity of the spectrophotometer values, while remaining high enough to give maximum separation of absorbance values for the three sample types. Sample volume of 20 μL gave HbA sample absorbance values of approximately 1.3, which accomplished both goals.

When Citrate Phosphate Buffer Solution was serially diluted three times and each dilution tested to determine the optimal buffer concentration, it was found that absorbance values of the three sample types were not clearly delineated using the diluted solutions. The original concentration, however, produced high HbA absorbance values, mid-range HbA+HbF absorbance values, and low HbF absorbance values, each being easily distinguishable from the others. Therefore, buffer concentration of 0.07 M sodium citrate and 0.06 M sodium phosphate, as stated in the Fetal Hemoglobin kit, was used in the final procedure.

Evaluation of Linearity

A confirmation of linearity was performed multiple times both on a single day (intra-run variability) and across different days (inter-run variability) to verify reproducibility, which was confirmed by low standard deviations for each sample type both within and across days. The distinct differences in absorbance values of HbA, HbA+HbF, and HbF samples were shown to be statically significant by low p-values of the ANOVA and Tukey's HSD. Testing a series of HbA:HbF blood mixtures in 10% increments showed a linear relationship between absorbance value and HbA level and an inverse linear relationship between absorbance value and HbF level. The coefficient of determination (r2) of 0.99 indicates that 99% of variability in absorbance values could be accounted for by variation of the HbA:HbF ratios. Visual inspection of the agarose electrophoresis supported the expected relative concentrations of HbA and HbF in the mixtures tested. (FIG. 2)

Throughout the study, visual observations of supernatant color supported the absorbance value readings. The size and color of the RBC pellets produced after centrifugation also followed the same logic. The smaller size and lack of red color of the 3-mm pellet in the HbA tubes, along with dark brown supernatant, represented nearly complete elution of hemoglobin from the RBCs. Conversely, the larger size and red color of the 5-mm pellet and the pale to colorless supernatant in the HbF tubes represented minimal HbA elution. As expected, the red-brown 4-mm pellet and medium-brown supernatant color in the 50:50 HbA+HbF tubes fell between the pellet size and supernatant color of the HbA and HbF tubes.

Example 1 demonstrated that the method may be used to determine levels of HbA in blood samples from normal human individuals also containing HbF and that this relationship is linear. Example 2 confirms these results, and further demonstrates that this method is equally effective at measuring HbS in blood samples from sickle individuals also containing HbF.

Example 2

Materials and Methods

Standardizing the Hematocrit

Microhematocrit was performed on each normal blood, cord blood, and sickle cell blood in order to adjust these three samples to have the same hematocrit as the highest sample. This standardizes the blood inoculum introduced into the test system. Once the highest hematocrit value was determined, the other two samples were adjusted to the same hematocrit value by removing plasma.

Hemoglobin F Procedure

Citrate Phosphate buffer solution was prepared as directed by the package insert to a final concentration of 0.07M sodium citrate, 0.06M sodium phosphate. Four milliliters of this solution was pipetted into 12×75 mm test tubes appropriately labeled. The test tubes were placed into the heat block incubator for 6 minutes to pre-warm to 37° C. Then 20 µl of the normal blood sample (HbA), a mixture of normal and cord blood (Hb A+HbF), or cord blood (HbF), adjusted to the same hematocrit, were added to a separate tube of buffer solution. Each tube was capped and inverted three times and incubated at 37° C. for 15 minutes in the heat block. After incubation, caps were removed without inverting the tubes, and the tubes were placed in the serofuge to pellet the RBCs. The eluted HbA was retained in the supernatant. Variation in supernatant color and pellet size were observed and recorded. Three milliliters of each supernatant was transferred into clean labeled 12×75 glass tubes, avoiding the RBC pellet. The absorbance of the supernatant was measured using the spectrophotometry at 395 nm.

Experimental Design

The HbF procedure previously developed in our lab was applied to three different experimental designs in which a tube of cord blood is compared to a tube of patient sample and one or more tubes containing some mixture of patient sample and cord blood. Three experimental designs were tested as follows:

Three tubes (AA, cord blood (F) and 50:50 AF mixture)
Three tubes (SS, cord blood (F) and 50:50 SF mixture)

Graduated mixtures of cord blood and a sickle cell patient sample (SS) in 10% increments as follows: 100% F, 90% F:10% S, 80% F:20% S, etc ending in 100% S Absorbance of the supernatant directly measures the HbA or HbS eluted from the sample. The difference between the total absorbance and the absorbance of the supernatant equals the HbF level.

Statistical Analysis

Using the statistical software SPSS 17.0, reproducibility data was analyzed to determine the mean and standard deviation of the absorbance values for the HbA, HbA+HbF, and HbF samples. One way ANOVA test and Tukey HSD post hoc test were performed to test for significant differences between the mean absorbance values of each sample type. Using correlation statistics, the absorbance values of HbS:HbF ratios from two runs were plotted and computed to determine linearity and reported using the correlation coefficients (r and r2).

Results

Example 2 demonstrated a similar reproducibility of the results observed in Example 1, and validates it use for determining HbS and HbF values from sickle cell individuals.

Figure 3:
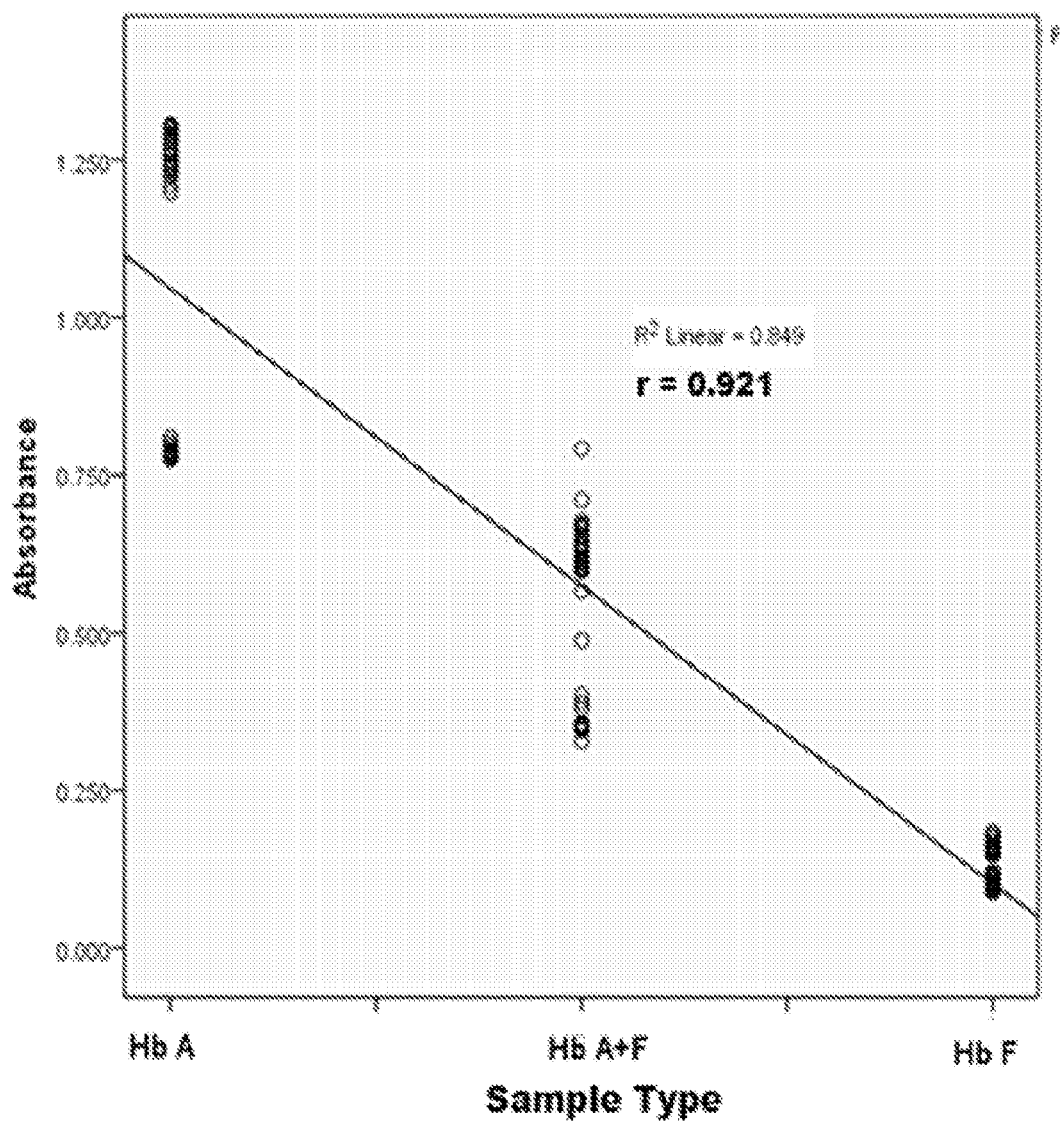
FIG. 3 illustrates absorbance values of blood containing HbA, HbA+HbF and HbF.

Example 2 compared the absorbance values of a test samples containing HbF (cord blood), HbA (normal blood), and a 50:50 mixture of HbF and HbA. The expected result was a high absorbance value in the supernatant of the HbA sample, a low absorbance value with the HbF tube and an intermediate absorbance value on a 50:50 mixture of HbF and HbA which reflects the relative elution of HbA from the three tubes. The means and standard deviations of the absorbance of the three different sample types (HbA, HbA+HbF, HbF) from 8 experiments are shown in Table 2. A one-way ANOVA was used to compare the mean values of the three groups and produced a P value of <0.0001. Since the ANOVA produced a statistically significant result, the Tukey HSD post hoc test was used to determine which pairs of mean absorbance values were statistically different. The Tukeys test showed statistical differences between each of the mean absorbance values, expressing a P value of <0.0001 for each sample pair (Table 2A). In addition, controls were performed along with the experiment to validate the results. A water control was used to determine to highest possible absorbance value should 100% of the hemoglobin be eluted from all the RBCs (Total Hemoglobin). A saline control was used to determine the background absorbance which would reflect the lowest possible absorbance if no hemoglobin was eluted from the sample. These controls were performed for both the HbF and HbA tubes. The mean absorbance of HbA in water was 1.368 and 0.032 in saline whereas the mean absorbance of HbF in water was 1.259 and 0.036 in saline (Table 2B). As shown by the linear regression (R2=0.849) in FIG. 3, as HbA concentration increases, the absorbance of the supernatant increases proportionately. This is inversely proportional to the HbF level.

TABLE 2A

Mean Absorption Values for HbA Elution using HbA, HbA + HbF, and HbF sample

| Exp # | N | Hb A Mean Absorbance | Hb A + F Mean Absorbance | Hb F Mean Absorbance |
|---|---|---|---|---|
| Exp 1 | 8 | 0.785 | 0.356 | 0.158 |
| Exp 2 | 8 | 0.790 | 0.36 | 0.165 |
| Exp 3 | 8 | 1.248 | 0.613 | 0.111 |
| Exp 4 | 8 | 1.288 | 0.659 | 0.104 |
| Exp 5 | 8 | 1.25 | 0.624 | 0.103 |
| Total | 40 | | | |
| Mean | | 1.072 | 0.522 | 0.128 |
| SD | | 0.237 | 0.143 | 0.03 |
| variance | | 0.056 | 0.02 | 0.001 |
| One-Way ANOVA Tukey HSD Post Hoc | | P value <0.0001 | | |
| 1. A; A + F | | P value <0.0001 | | |
| 2. A; F | | P value <0.0001 | | |
| 3. A + F; F | | P value <0.0001 | | |

TABLE 2B

Controls (100% and 0%) for HbA and HbF samples

| Diluents Type | N | Hb A Mean absorbance | Hb F Mean absorbance |
|---|---|---|---|
| Water (100%) | 5 | 1.368 | 1.259 |
| Saline (0%) | 5 | 0.032 | 0.036 |

Determining HbS in Samples from Sickle Cell Individuals

Figure 4:
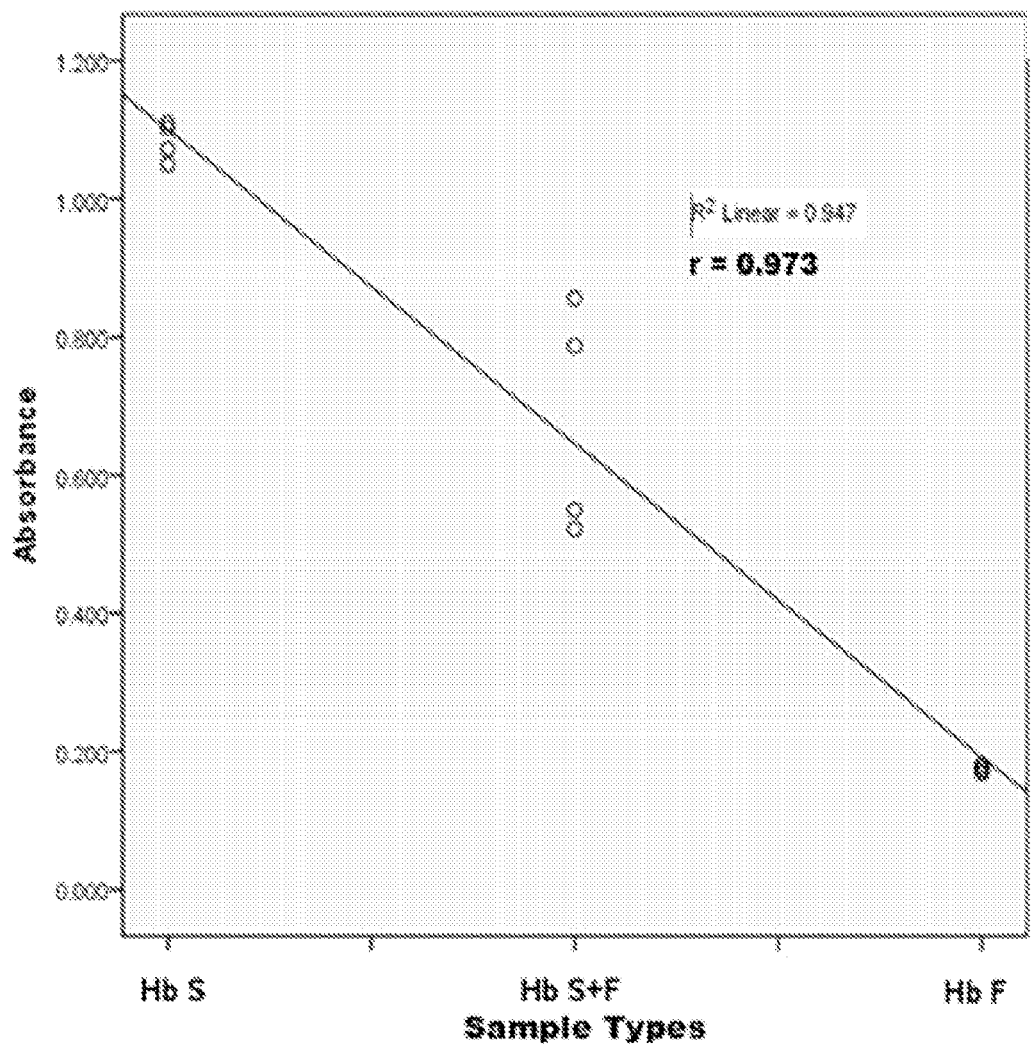
FIG. 4 illustrates absorbance values of blood containing HbS, HbS+HbF and HbF.

In order to confirm that HbS elutes from RBCs in the same manner as HbA, and that the utility of the method extends to determining HbS and HbF in samples containing both HbS and HbF, such as samples form sickle cell individuals undergoing hydroxyurea treatment, the above determination of HbA was repeated, while substituting blood from sickle cell patients for the blood from normal adults. It was visually apparent that the color of the supernatant was more intense in the HbS tube, intermediate in the HbS:HbF tube and less intense in the HbF tube. In addition, the diameter of the RBC containing pellet after centrifugation was 2 mm and brown, in the HbS sample; 5 mm and dark red-brown in the HbS+HbF sample; and 7 mm and dark red in the HbF sample. Indicating an increase in size and increased red color of the pellet, with increasing amounts of HbF in the sample. The mean absorbance values across the 4 experiments and the corresponding standard deviations were: HbS mean=1.084 (SD 0.028), HbS+HbF mean=0.679 (SD 0.168), and HbF mean=0.175 (SD 0.005) (Table 3A). In experiment #2, the sample size was too small to perform ANOVA test. The linear regression (R2=0.947) curve in FIG. 4 shows that as HbS concentration increases, the absorbance of the supernatant increases which is inversely proportional to the HbF concentration.

TABLE 3A

Mean Absorption Values for HbS Elution using HbS, HbS + HbF, and HbF samples.

| Exp # | N | HbS Mean Absorbance | HbS + F Mean Absorbance | HbF Mean Absorbance |
|---|---|---|---|---|
| Exp 1 | 2 | 1.061 | 0.822 | 0.179 |
| Exp 2 | 2 | 1.106 | 0.536 | 0.171 |
| Total Mean | 4 | 1.084 | 0.679 | 0.175 |
| SD | | 0.028 | 0.168 | 0.005 |
| Variance | | 0.001 | 0.028 | 0.000 |
| One WAY ANOVA | | Did not perform; insufficient N | | |
| Tukey HSD Post Hoc | | Did not perform; insufficient N | | |

TABLE 3B

Controls (100% and 0%) using HbS and HbF samples

| Diluents Type | N | HbS Mean absorbance | HbF Mean absorbance |
|---|---|---|---|
| Water (100%) | 5 | 1.161 | 1.291 |
| Saline (0%) | 5 | 0.059 | 0.047 |

Linearity of HbS Determinations

Figure 6:
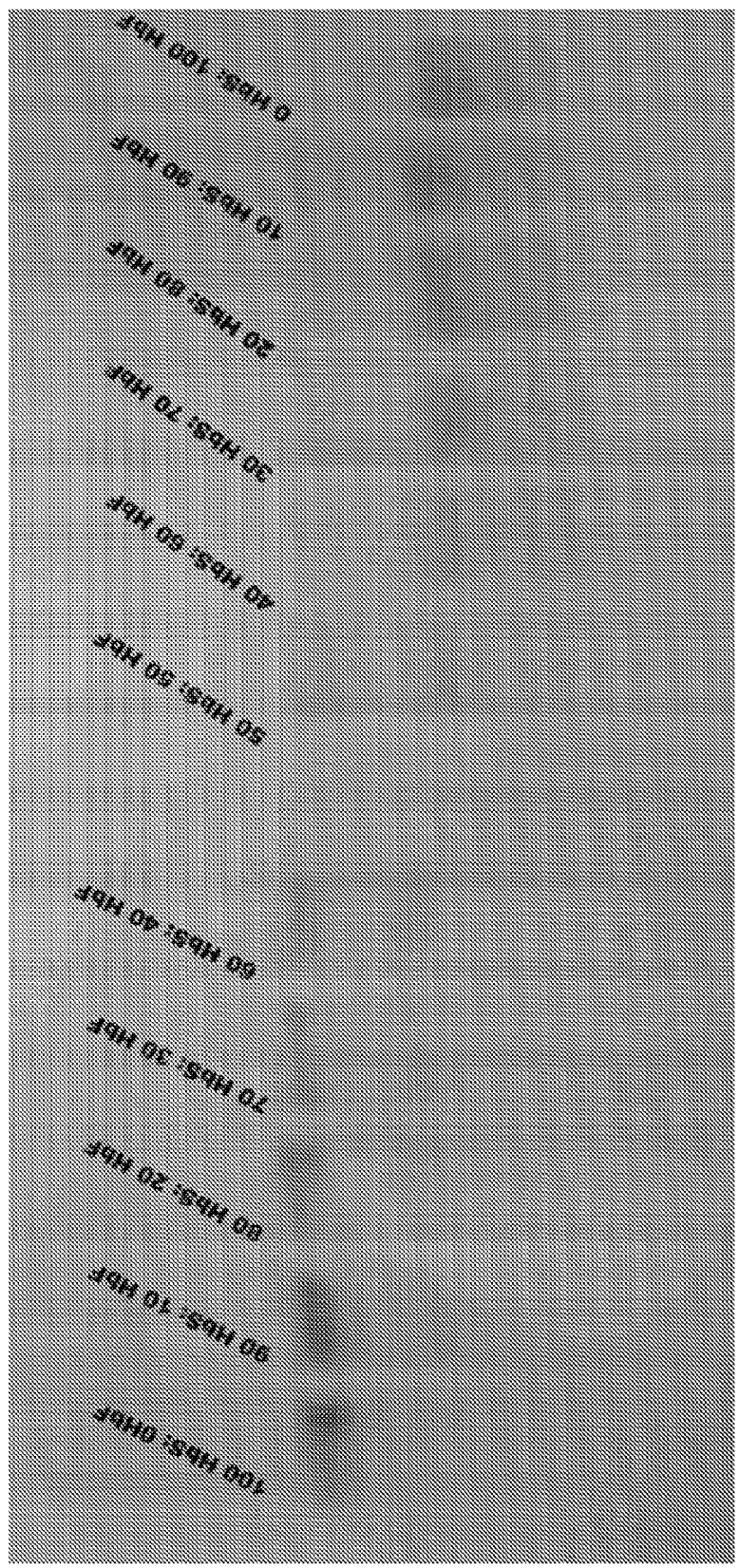
FIG. 6 illustrates gel electrophoresis of HbS:HbF ratio samples.

The Inventors were able to confirm a linear relationship in absorbance values in a series of samples containing a mixture HbS and HbF containing blood, in increasing ratio, in increments of 10 percent. There was a visually observable variation in color of the supernatants of eleven different HbS:HbF samples. The color intensity is gradually decreasing from tube #1 (100% HbS and 0% HbF tube) to tube #11 (0% HbS and 100% HbF). The linear regression curve in figured 5 shows that as the percentage of HbS decreases, the absorbance of the supernatant also decreases. In addition, agarose gel electrophoresis confirmed that the mixtures of cord blood and sickle cell blood contained the expected amounts of HbS and HbF, and do represent a gradual decrease in HbS and the proportional increase in HbF in 10% increments based on banding intensity. (FIG. 6)

TABLE 4A

Absorbance Values of samples with decreasing HbS percentage and increasing HbF percentage.

| Sample type | Exp 1 | Exp 2 | Exp 3 | Exp 4 | Exp 5 | Exp 6 | Exp 7 | Exp 8 | Mean | Stddev | Variance |
|---|---|---|---|---|---|---|---|---|---|---|---|
| 100HbS: 0 HbF | 0.955 | 1.104 | 0.966 | 1.137 | 0.912 | 1.128 | 0.968 | 0.943 | 1.01 | 0.09 | 0.01 |

TABLE 4A-continued

Absorbance Values of samples with decreasing
HbS percentage and increasing HbF percentage.

| Sample type | Absorbance | | | | | | | | Mean | Stddev | Variance |
|---|---|---|---|---|---|---|---|---|---|---|---|
| | Exp 1 | Exp 2 | Exp 3 | Exp 4 | Exp 5 | Exp 6 | Exp 7 | Exp 8 | | | |
| 90HbS: 10 HbF | 0.891 | 0.98 | 0.817 | 1.126 | 0.901 | 1.006 | 0.956 | 0.931 | 0.95 | 0.09 | 0.01 |
| 80HbS: 20HbF | 0.838 | 0.804 | 0.633 | 1.016 | 0.858 | 0.896 | 0.826 | 0.767 | 0.83 | 0.11 | 0.01 |
| 70HbS: 30 HbF | 0.745 | 0.708 | 0.585 | 0.919 | 0.83 | 0.738 | 0.714 | 0.605 | 0.73 | 0.11 | 0.01 |
| 60HbS: 40 HbF | 0.641 | 0.653 | 0.485 | 0.81 | 0.712 | 0.613 | 0.662 | 0.527 | 0.64 | 0.10 | 0.01 |
| 50HbS: 50 HbF | 0.605 | 0.471 | 0.366 | 0.677 | 0.649 | 0.59 | 0.578 | 0.401 | 0.54 | 0.12 | 0.01 |
| 40HbS: 60 HbF | 0.512 | 0.421 | 0.259 | 0.509 | 0.524 | 0.414 | 0.417 | 0.337 | 0.42 | 0.10 | 0.01 |
| 30HbS: 70 HbF | 0.469 | 0.333 | 0.196 | 0.406 | 0.448 | 0.321 | 0.338 | 0.274 | 0.35 | 0.09 | 0.01 |
| 20HbS: 80 HbF | 0.405 | 0.316 | 0.18 | 0.215 | 0.301 | 0.216 | 0.239 | 0.228 | 0.26 | 0.07 | 0.01 |
| 10HbS: 90 HbF | 0.268 | 0.241 | 0.125 | 0.201 | 0.22 | 0.188 | 0.2 | 0.181 | 0.20 | 0.04 | 0.002 |
| 0HbS: 100 HbF | 0.183 | 0.170 | 0.099 | 0.106 | 0.108 | 0.117 | 0.103 | 0.100 | 0.12 | 0.03 | 0.001 |

TABLE 4B

Controls using SS samples with different diluents.
Controls

| Diluents Type | N | Hb S Mean absorbance |
|---|---|---|
| Water (100%) | 8 | 1.180 |
| Saline (0%) | 8 | 0.048 |

Discussion

These examples demonstrate that HbA can be selectively eluted from RBCs using a citrate buffer solution while HbF is selectively retained. Also that HbA may be quantitated in order to calculate levels of HbF. These results are statistically significant as demonstrated by the AVOVA and Tukey test results. The SD of each of the three sample types (HbA, HbA+HbF, and HbF) was very small indicating that the method is very reproducible between runs. In addition, a linear regression curve indicated a linear relationship between the three samples where HbA eluted from the RBCs into acidic buffer producing higher absorbance values, whereas HbF showed resistance or minimal elution into the acid solution resulting in lower absorbance values.

Example 2 confirms that the method may be used to measure HbS and calculate HbF from samples from sickle cell patients. When sickle cell blood containing HbS is substituted for normal blood containing HbA, these results demonstrate that HbS selectively elutes from RBCs in the same manner and as efficiently as was observed for HbA. The examples also demonstrate that HbS levels may be quantified in the presence of HbF. As anticipated, the highest levels of HbS in the supernatant provided the highest absorbance values while supernatant from cells containing mostly HbF tube showed the lowest absorbance. Furthermore, visual observations confirmed these results. As expected, the HbS:HbF mixture was intermediate in color intensity between samples containing only HbS or HbF. In addition, the size and color of pellets were also indicators that selective elution of HbS had occurred. The greater amount of HbF, the larger the pellet size and darker color, as a consequence of HbF remaining with RBCs in the pellet. In contrast small, brown pellets observed in the HbS tubes represented nearly complete elution of hemoglobin from the RBCs.

Figure 5:
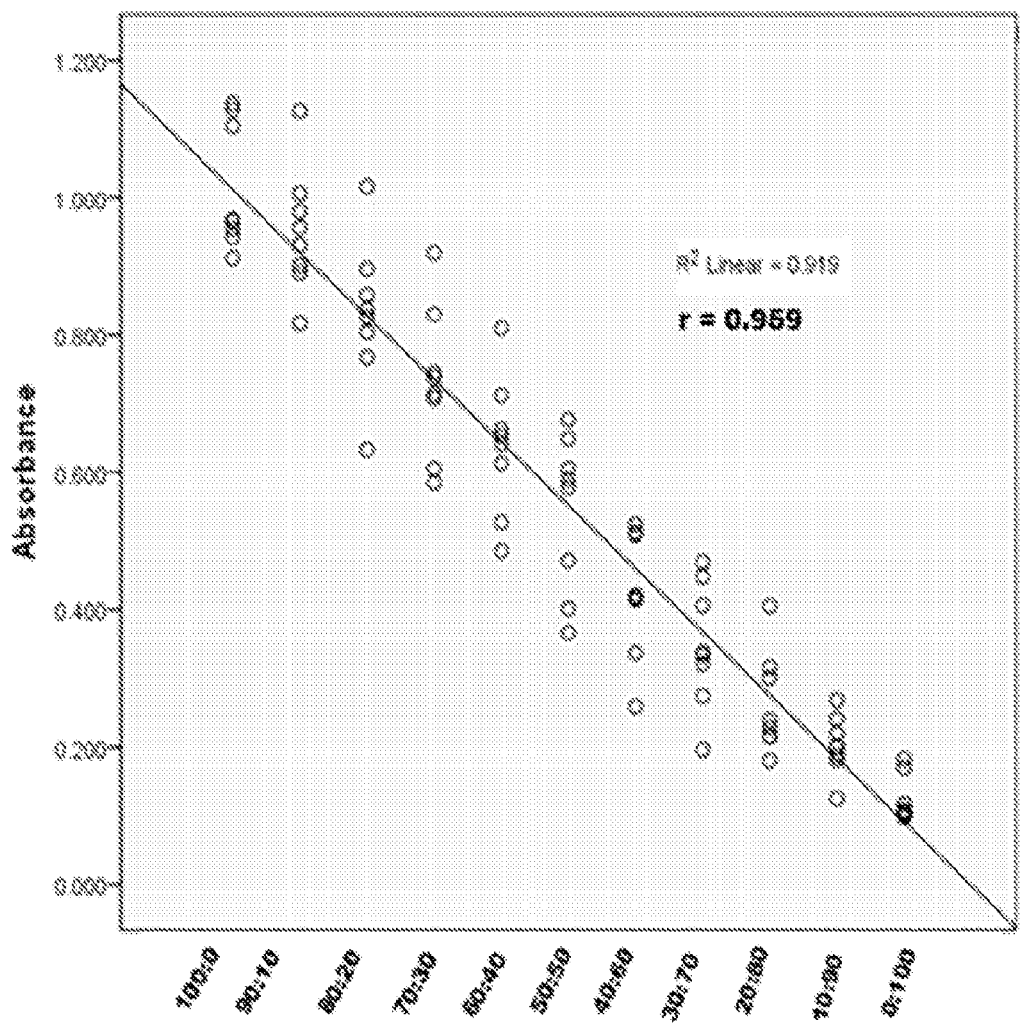
FIG. 5 illustrates absorbance values of samples with decreasing HbS percentage and increasing HbF percentage.

When comparing combinations of HbS:HbF blood in known ratios, the results demonstrated a linear relationship between the absorbance value and HbS percentage, and an inverse linear relationship between the absorbance value and HbF percentage, with a coefficient of determination (r2) of 0.919 (FIG. 5). Furthermore, the composition of hemoglobin in each sample was confirmed by agarose gel electrophoresis. These results demonstrate a linear relationship between HbS percentage and absorbance indicating a reproducible and selective elution of HbS from RBCs, as well as retained HbF intracellularly. Since the absorbance of the supernatant, is a reliable indicator of HbS, and is inversely proportional to levels of HbF, a HbS determination in a sample from a patient with sickle cell anemia undergoing hydroxyurea treatment, can be used to determine levels of HbF levels by either calculating HbF using total hemoglobin levels (HbF=Total Hemoglobin−HbS), or by standardizing the blood volume introduced into the test system. Either method will allow a treating physician to determine HbF levels to differentiate hydroxyurea responders from non-responders and to monitor HbF levels in responders.

The methods disclosed by the Inventor may be used to quantify HbA, HbS, and HbF concentrations in the blood of normal and sickle cell patients. It is simple and inexpensive enough for use in under-developed countries. It provides a means for physicians to monitor HbF levels in a patient receiving hydroxyurea treatment for sickle cell anemia.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The invention claimed is:

1. A method for determining the amount of fetal hemoglobin in an individual with sickle cell anemia undergoing hydroxyurea treatment, comprising:
   a) providing a first sample from the individual comprising red blood cells and a second sample of equal volume from the individual comprising red blood cells;
   b) adding the first sample to a buffer solution to form a first mixture, the buffer solution comprising an acidic buffer with a pH in a range of about 3.1 to about 3.5;
   c) incubating the first mixture for a sufficient time to maximize elution of sickle cell hemoglobin, and minimize elution of fetal hemoglobin,
   d) subjecting the first mixture to centrifugation sufficient to form a solid deposit and a first supernatant;
   e) determining an optimum wavelength to measure maximum absorbance of sickle cell hemoglobin of the first supernatant;
   f) determining an absorbance value of the first supernatant at the optimum wavelength, and determining a percentage of sickle hemoglobin from a standard reference curve representing absorption values versus decreasing percentage of sickle cell hemoglobin and increasing percentage of fetal hemoglobin;
   g) adding the second sample to deionized water to form a second mixture;
   h) incubating the second mixture for a sufficient time for 100 percent hemolysis of the red blood cells;
   i) subjecting the second mixture to centrifugation sufficient to form a solid deposit and a second supernatant;
   j) determining an optimum wavelength to measure maximum absorbance of total hemoglobin of the second supernatant, or selecting the optimum wavelength determined in step e) to use in step k);
   k) determining an absorbance value of the second supernatant at the optimum wavelength from in step j) and assigning the absorbance value of the second supernatant to represent total hemoglobin for the individual; and
   l) determining a percentage of Fetal hemoglobin in the individual's blood by subtracting the percentage of sickle hemoglobin from the total hemoglobin for the individual.

2. The method of claim 1, wherein the acidic buffer consists of citrate phosphate buffer.

3. The method of claim 2, wherein the citrate phosphate buffer has a concentration of about 0.07 M sodium citrate and about 0.06 M sodium phosphate.

4. The method of claim 1, wherein the acidic buffer has a pH range of about 3.1 to about 3.3.

5. The method of claim 1, wherein the acidic buffer has a pH of about 3.3.

6. The method of claim 1, wherein incubating the first mixture for a sufficient time consists of incubating the first mixture for about 5 minutes to about 7 minutes.

7. The method of claim 1, wherein incubating the first mixture for a sufficient time consists of incubating the first mixture for about 6 minutes.

8. The method of claim 1, wherein incubating the first mixture is conducted at a temperature of about 37° C.

9. The method of claim 1, wherein subjecting the first mixture to centrifugation consist of centrifuging the first mixture for a minimum amount of time or greater required to produce a solid pellet of red blood cells.

10. The method of claim 1, wherein subjecting the first mixture to centrifugation consists of centrifuging the first mixture at 3400 revolutions per minute for about 30 seconds.

11. The method of claim 1, wherein determining the optimum wavelength of the first or second supernatant, consists of measuring the absorbance of the first or second supernatant at range of wavelengths and selecting the wavelength which indicates maximum absorbance for said supernatant, or for both first and second supernatants.

12. The method of claim 1, wherein the optimum wavelength of the first or second supernatant is from about 375 nm to about 415 nm.

13. The method of claim 1, wherein the optimum wavelength of the first or second supernatant is from about 393 nm to about 397 nm.

14. The method of claim 1, wherein the optimum wavelength of the first or second supernatant is about 395 nm.

15. The method of claim 1, wherein the reference curve representing absorption values versus decreasing percentage of sickle cell hemoglobin and increasing percentage of Fetal hemoglobin consists of a curve as set forth in FIG. 4.

16. The method of claim 1, wherein the reference curve representing absorption values versus decreasing percentage of sickle cell hemoglobin and increasing percentage of Fetal hemoglobin consists of the curve set forth in FIG. 5.

17. A method for determining Fetal hemoglobin in a subject in an individual with sickle cell anemia, comprising:
   a) providing a sample from the individual comprising red blood cells;
   b) determine a volume of the sample containing a known amount of total hemoglobin;
   c) adding the volume to an acidic buffer, to form a mixture;
   d) subjecting the mixture to centrifugation to form a solid deposit and a supernatant;
   e) taking an absorbance reading of the supernatant, and
   f) comparing the absorbance reading to a reference curve representing absorption values versus decreasing percentage of sickle cell hemoglobin and increasing percentage of fetal hemoglobin to determine the relative amounts of HbS and Fetal hemoglobin in the sample from the known amount of total hemoglobin.

18. The method of claim 17, wherein a hematocrit or hemoglobin determination is used to determine a blood volume containing a known amount of total hemoglobin.

19. A method for determining the percentage of sickle hemoglobin in an individual with sickle cell anemia, comprising:
   a) providing a sample from the individual comprising red blood cells;
   b) adding the sample to a buffer solution to form a mixture, the buffer solution comprising an acidic buffer with a pH in the range of about 3.1 to about 3.5;

c) incubating the mixture for a sufficient time to maximize elution of sickle cell hemoglobin, and minimize elution of fetal hemoglobin,
d) subjecting the mixture to centrifugation sufficient to form a solid deposit and a supernatant;
e) determining an optimum wavelength to measure maximum absorbance of sickle cell hemoglobin of the supernatant; and
f) determining an absorbance value of the supernatant at the optimum wavelength, and determining the percentage of sickle hemoglobin from a standard reference curve representing absorption values versus decreasing sickle cell hemoglobin percentage and increasing fetal hemoglobin percentage.

20. A method for determining the amount of adult hemoglobin in an individual, without sickle cell anemia, comprising:
a) providing a sample from the individual comprising red blood cells;
b) adding the sample to a buffer solution to form a mixture, the buffer solution comprising an acidic buffer with a pH in a range of about 3.1 to about 3.5;
c) incubating the mixture for a sufficient time to maximize elution of adult cell hemoglobin, and minimize elution of fetal hemoglobin,
d) subjecting the mixture to centrifugation sufficient to form a solid deposit and a supernatant;
e) determining an optimum wavelength to measure to measure maximum absorbance of adult hemoglobin of the supernatant;
f) determining an absorbance value of the supernatant at the optimum wavelength, and determining the amount of adult hemoglobin from a standard reference curve representing absorption values versus decreasing adult hemoglobin and increasing fetal hemoglobin.

\* \* \* \* \*